(12) United States Patent
Bley

(10) Patent No.: US 7,266,991 B2
(45) Date of Patent: Sep. 11, 2007

(54) SENSOR FOR HELIUM OR HYDROGEN

(75) Inventor: Werner Grosse Bley, Bonn (DE)

(73) Assignee: Inficon GmbH, Cologne (DE)

( * ) Notice: Subject to any disclaimer, the term of this patent is extended or adjusted under 35 U.S.C. 154(b) by 689 days.

(21) Appl. No.: 10/297,571

(22) PCT Filed: May 25, 2001

(86) PCT No.: PCT/EP01/02970

§ 371 (c)(1),
(2), (4) Date: Apr. 21, 2003

(87) PCT Pub. No.: WO02/03057

PCT Pub. Date: Jan. 10, 2002

(65) Prior Publication Data

US 2003/0159929 A1    Aug. 28, 2003

(30) Foreign Application Priority Data

Jun. 30, 2000  (DE) ................................. 100 31 882

(51) Int. Cl.
*G01N 7/00* (2006.01)
(52) U.S. Cl. ........................................ 73/31.05; 73/23.2
(58) Field of Classification Search ............... 73/31.05, 73/23.2; 324/464
See application file for complete search history.

(56) References Cited

U.S. PATENT DOCUMENTS

| 2,988,657 | A | * | 6/1961 | Winfried et al. ............... 417/49 |
| 3,051,868 | A | * | 8/1962 | Redhead ...................... 315/108 |
| 4,307,323 | A | * | 12/1981 | Bills et al. .............. 315/111.91 |
| 4,477,778 | A | | 10/1984 | Lawrence, Jr. et al. |
| 5,661,229 | A | * | 8/1997 | Bohm et al. .................. 73/40.7 |
| 6,277,177 | B1 | * | 8/2001 | Bley et al. ....................... 96/4 |

FOREIGN PATENT DOCUMENTS

| DE | 43 26 267 A1 | 2/1995 |
| EP | 0 352 371 A2 | 1/1990 |
| EP | 0 352 371 A3 | 5/1990 |
| WO | 02/03057 A1 | 1/2002 |

* cited by examiner

*Primary Examiner*—Hezron Williams
*Assistant Examiner*—Rodney Frank
(74) *Attorney, Agent, or Firm*—Marjama Muldoon Blasiak & Sullivan LLP

(57) ABSTRACT

The invention relates to a sensor (1) for helium or hydrogen with a vacuum-tight housing (2), wherein a gas consuming cold cathode array (3, 4) is arranged, in addition to a selectively active passage (9) for the gas to be detected. According to the invention, in order to improve the properties of said sensor, the housing (2) is made of glass, components of the gas passage (9) include a membrane (18) made of a silicon material having the desired selective qualities, in addition to a silicon plate (19) which supports the membrane (18) and is provided with a plurality of openings (21) and a heating element (24). The housing (2) and the selectively active gas passage (9) are joined together without polymer and elastomer.

6 Claims, 1 Drawing Sheet

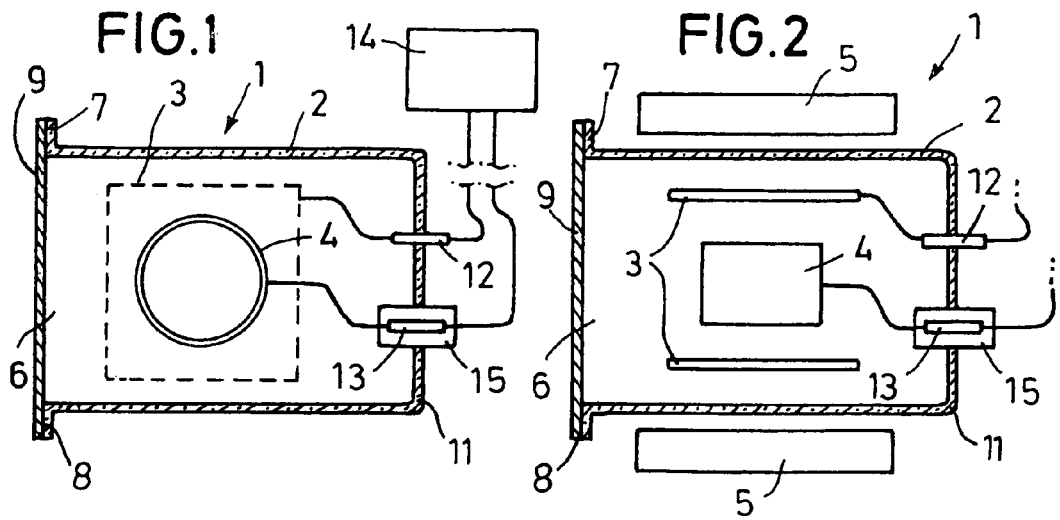
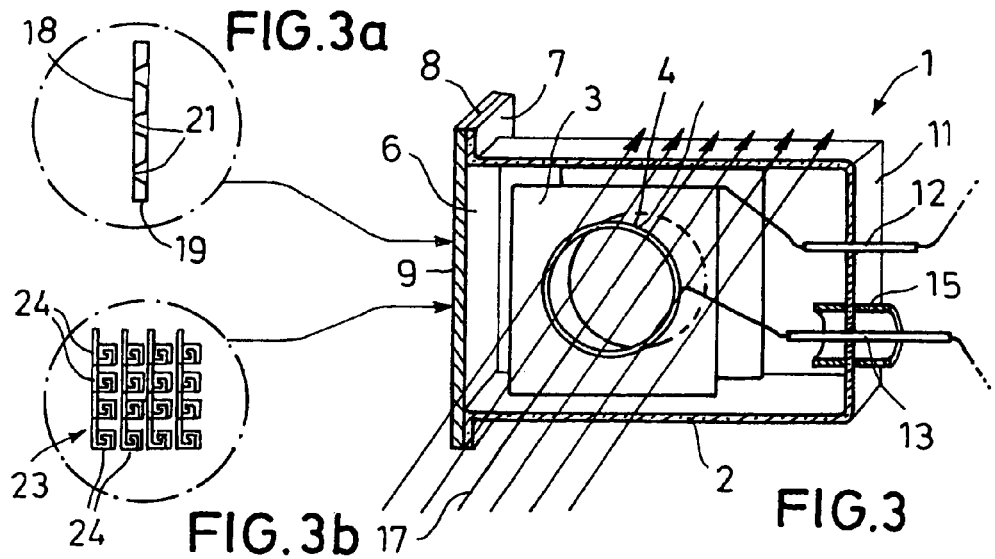
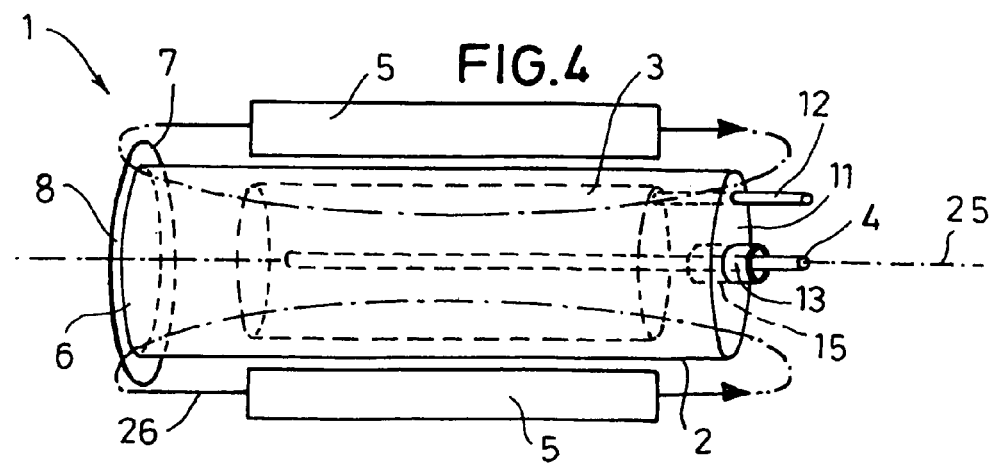

SENSOR FOR HELIUM OR HYDROGEN

CROSS REFERENCE TO RELATED APPLICATIONS

This application claims priority of German patent 100 31 882.7 filed on Jun. 30, 2000 and also claims priority of PCT/EP 01/02970 filed on Mar. 15, 2001.

1. Field of Invention

The present invention relates to a sensor for helium or hydrogen with a vacuum-tight housing, wherein a gas consuming cold cathode array is arranged, in addition to a selectively active passage for the gas to be detected.

2. Background of the Invention

From DE-A 43 26 265 a sensor having these characteristics is known. Sensors of this kind are of a relatively simple design and may be operated approximately up to atmospheric pressure (outside their housing). Still, sensors of this kind have not been able to penetrate the market in particular because they are, compared to the commonly employed but more costly mass spectrometers, too insensitive and can for this reason not be employed under vacuum conditions at low partial pressures of the test gas.

SUMMARY OF THE INVENTION

It is the task of the present invention to create a sensor of the kind mentioned above having improved properties. This task is solved through the present invention by the characterising features of the patent claims.

In that the housing is made of glass, $H_2$ gas is not outgassed within the housing. Preferably borosilicate glass is employed since it is suited for both fusing with correspondingly thermally adapted metals as well as anodic bonding or diffusion welding with silicon. The passage (as is basically known from DE-A-195 21 275) employed in the sensor according to the present invention permits the arrangement of a gas passage having a relatively large surface area of sufficient stability. Finally the joint of the gas passage with the housing by means of anodic bonding which is free of polymer and elastomer offers the advantage that no outgassing into the inside of the housing is effective originating from seals or adhesives. All these measures are beneficial with respect to the sensor's sensitivity and result in an improved detection limit.

BRIEF DESCRIPTION OF THE DRAWINGS

Further advantages and details of the present invention shall be explained with reference to the examples of embodiments depicted schematically in drawing FIGS. 1 to 4. Depicted are/is in drawing FIGS. 1 to 3 depicts an embodiment of the invention with a substantially cuboid housing; and drawing FIG. 4 depicts an embodiment of the invention having the geometrical arrangement of a magnetron.

DETAILED DESCRIPTION

In all drawing figures the housing of the sensor 1 is designated as 2, the cathode components accommodated within the housing 2 as 3, and the anode components as 4, and the magnets located outside of the housing 2 are designated as 5. The otherwise closed housing 2 is open on its respective face sides 6. In this area it is equipped with a flange-like rim 7, the annular surface 8 on the face side serving the purpose of providing the joint between a gas passage 9 (shown only depicted in drawing FIGS. 1 to 3) with the housing 2 by means of anodic bonding or diffusion welding. The face side 11 of the housing 2 opposite the open face side 6 i.e., the side opposite the gas passage 9 is equipped with electric feedthroughs 12 and 13 which are linked via lines to a control, measuring, recording, display and/or power supply unit depicted only as block 14. Feedthrough 12 serves the purpose of supplying the cathode components 3 with high tension. Feedthrough 13 links the anode 4 to the unit 14. Said feedthrough 13 is equipped with a shield 15, since the fed-through line serves the purpose of supplying extremely low ion currents (down in to the fA range) to unit 14. As the materials for the feedthroughs 12, 13 and for shield 15, iron (cobalt)/nickel alloys (trade names VACON, KOVAR, . . . ) have been found to be the most expedient. Tungsten and platinum may under special circumstances also be employed together with special types of glass.

In the embodiments depicted in drawing FIGS. 1 to 3 the housing 2 has substantially the shape of a cuboid. Located within the housing 2 are an annular anode 4 made of stainless steel and two approximately square cathodes 3 preferably made of titanium sheet sections which are fitted in front of the face sides of the annular cathode 3 in the usual manner. For the purpose of minimising degassing of hydrogen, the electrodes have been annealed at approximately 600° C. to 900° C. in a high-vacuum degassing process.

Drawing FIG. 3 is a perspective view. The housing wall facing the viewer is missing. The magnetic field produced by the magnets 5, preferably permanent magnets, is indicated by arrows 17.

Drawing FIG. 3. comprises two enlarged views 3a and 3b for the gas passage 9. Drawing FIG. 3a depicts a sectional view through the gas passage 9. It is composed substantially of a membrane 18 with the desired selective properties and a carrier 19. The carrier 19 is a silicon plate, which is provided with a plurality of openings 21 produced with the aid of known etching methods. The openings 21 form windows closed by the membrane 18 said windows having a surface area of 0.5 mm$^2$, for example. The sum of the window surfaces forms the actual gas passage (total penetration area).

The gas passage 9 may, for example, be manufactured based on a process as is known from DE-195 21 257 A1. The same also applies to the heater 23 with which the gas passage 9 is equipped for the purpose of increasing the response time. Drawing FIG. 3b depicts an embodiment in which each of the window surfaces is equipped with a heating filament on the outside, said filament made of nickel/chromium or preferably platinum 24. The heating filaments are supplied with electric power from the outer rim of the structure where on each narrow side one pole of each of the heating filaments is joined to the others.

In the embodiment in accordance with drawing FIG. 4 the housing 2 and the cathode 3 are designed to be cylindrical in shape.

The anode 4 has the shape of a rod which is arranged along the joint axis 25 of housing 2 and cathode 3. The lines of magnetic flux produced by the magnet 5 are marked by arrows 26.

Through the measures in accordance with the present invention it shall be achieved that no degassing is effected into the housing 2, so as to attain a level of partial pressure sensitivity comparable to mass spectrometers. Since it is required to match; provide a tight seal between the housing 2 made of, for example, borosilicate glass and other materials, it is expedient that different areas of the housing 2 be made of different types of glass having different coefficients of expansion. Thus there exists the possibility of adapting the coefficient of expansion of the housing at the point where it needs to be joined to an other material to the coefficient of expansion of the other material. The sealing properties of the housing 2 are thus improved, material tensions are reduced.

Through the measures in accordance with the present invention it shall be achieved that no degassing is effected into the housing 2, so as to attain a level of partial pressure sensitivity comparable to mass spectrometers. Since it is required to match resp. provide a tight seal between the housing 2 made of, for example, borosilicate glass and other materials, it is expedient that different areas of the housing 2 be made of different types of glass having different coefficients of expansion. Thus there exists the possibility of adapting the coefficient of expansion of the housing at the point where it needs to be joined to an other material to the coefficient of expansion of the other material. The sealing properties of the housing 2 are thus improved, material tensions are reduced.

For the purpose of adaptation to silicon having a thermal coefficient of expansion of 3.0 ppm/K, DURAN glass at 3.3 ppm/K is especially well suited. For matching to KOVAR or VACON, SCHOTT fusing glass 8250 at 5.0 ppm/K will provide an optimum solution. Besides this, matching platinum with thermometer glass is possible and in principle tungsten can be matched to DURAN. For the purpose of matching the different coefficients of expansion, a range of so-called transitional glass types is being offered which need to be employed in proper sequence when aiming at avoiding temperature induced strains and thus avoiding leaks or even damage.

In this embodiments depicted, for example the type of borosilicate glass employed in the area of the face side 6; the anodic bonding surface 8 for the housing 2 is matched to the coefficient of expansion of the silicon plate 19 carrying the selective membrane 18. In the area of the opposing face side 11, the type of borosilicate glass employed there for the housing 2 has expediently a coefficient of expansion which corresponds to that of the metals (KOVAR or VACON, for example) fed through at that point. In the transitional area between the face sides 6 and 11, a transitional type of glass is expediently employed having a coefficient of expansion between the two coefficients of expansion of the two types of glass which are employed at the respective face sides. If necessary also several transitional types of glass, the coefficients of expansion being grade in the same direction, may be employed for the purpose of avoiding strain within the materials. There thus result the following alternatives for production:

Housing made of DURAN glass (SCHOTT), current feedthroughs made of KOVAR or VACON fused in SCHOTT 8250 glass and matched with domes of transitional glass to DURAN, silicon disk with direct anodic bonding;

Housing of fused glass (SCHOTT 8250), current feedthroughs made of KOVAR or VACON, silicon disk with intermediate aluminum layer, diffusion welded;

Housing made of DURAN glass (SCHOTT), current feedthroughs made of tungsten, silicon disk with direct anodic bonding;

Housing made of DURAN glass (SCHOTT), current feedthroughs made of platinum fused in thermometer glass and matched with domes of transitional glass to DURAN, silicon disk with direct anodic bonding.

The types of glass stated are only to be taken as examples, decisive is in each instance matching of the coefficients of expansion between metal and glass.

The benefits of the sensor in accordance with the present invention are in particular that these may be operated approximately up to atmospheric pressure are that they are sufficiently sensitive. For this reason they may be employed instead of mass spectrometers for the purpose of detecting leaks, i.e. they may be a component of a test gas detector of leakage test instruments, independently of whether a test sample is connected to the leakage detector or the provision of a sniffer employed to scan the test object.

Also the employment in vacuum systems, for example involving continuously changing pressures is beneficial both as being a component of a test gas detector of the leakage detection facility or as a gas sensor in general. When searching for leaks on a vacuum chamber it is sprayed from the outside with the test gas. In the instance of a leakage, the test gas enters and is recorded by the sensor.

What is claimed is:

1. A gas detection sensor for detecting at least one of hydrogen and helium, said sensor comprising:
    a vacuum-tight housing;
    a gas consuming cold cathode array arranged in said housing; and
    a selectively active passage for the gas to be detected wherein said housing is made from glass, said selectively active passage including a membrane made from a silicon material having desired selective qualities, a silicon plate supporting said membrane, and a heating element, said silicon plate having a plurality of openings and in which said housing and said selectively active passage are joined together without use of polymers or elastomers wherein the housing and the selectively active passage are joined together by at least one of anionic bonding and diffusion welding in a high-vacuum tight manner and in which the housing consists of borosilicate glass.

2. A sensor according to claim 1, wherein the cathode of the cathode array consists of titanium plate.

3. A sensor according to claim 1, wherein a side of the housing facing away from the selectively active passage is equipped with voltage or current see-through.

4. A sensor according to claim 1, wherein said sensor is used for the purpose of leakage detection.

5. A sensor according to claim 1, wherein said sensor is a component of a test gas detector for a leakage detection instrument.

6. A sensor according to claim 1, wherein said sensor is employed in a vacuum system.

* * * * *

UNITED STATES PATENT AND TRADEMARK OFFICE
CERTIFICATE OF CORRECTION

PATENT NO. : 7,266,991 B2  
APPLICATION NO. : 10/297571  
DATED : September 11, 2007  
INVENTOR(S) : Werner Grosse Bley It is certified that error appears in the above-identified patent and that said Letters Patent is hereby corrected as shown below:

Col. 2, Line 65. Please delete the words "match; provide" and replace with --match; that is, provide--

Col. 3, Line 11. Please delete the words "match resp. provide" and replace with --match; that is, provide--

Col. 3, Line 34. Please delete the words "side 6; the" and replace with --side 6; that is, the--

Col. 3, Line 35. Please delete the words "housing 2 is" and replace with --housing 2, is--

Signed and Sealed this

Twenty-seventh Day of November, 2007

JON W. DUDAS  
*Director of the United States Patent and Trademark Office*